US012616524B2

(12) United States Patent
Lavrov et al.

(10) Patent No.: US 12,616,524 B2

(45) Date of Patent: May 5, 2026

---

(54) IMAGE-GUIDED NAVIGATION SYSTEM FOR TARGETED DELIVERY OF SPINAL CORD THERAPIES

(71) Applicant: Mayo Foundation for Medical Education and Research, Rochester, MN (US)

(72) Inventors: Igor A. Lavrov, Rochester, MN (US); Riazul Islam, Rochester, MN (US); Nirusha Lachman, Rochester, MN (US); Alan Mendez Ruiz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 32 days.

(21) Appl. No.: 17/770,007

(22) PCT Filed: Oct. 19, 2020

(86) PCT No.: PCT/US2020/056319

§ 371 (c)(1),
(2) Date: Apr. 18, 2022

(87) PCT Pub. No.: WO2021/077081

PCT Pub. Date: Apr. 22, 2021

(65) Prior Publication Data

US 2022/0387114 A1    Dec. 8, 2022

Related U.S. Application Data

(60) Provisional application No. 62/916,640, filed on Oct. 17, 2019.

(51) Int. Cl.
*A61B 34/20* (2016.01)
*A61B 5/107* (2006.01)
(Continued)

(52) U.S. Cl.
CPC ............ *A61B 34/20* (2016.02); *A61B 5/1072* (2013.01); *A61B 34/10* (2016.02); *A61B 34/25* (2016.02);
(Continued)

(58) Field of Classification Search
CPC ....... A61B 34/20; A61B 5/1072; A61B 34/10; A61B 34/25; A61B 90/37;
(Continued)

(56) References Cited

U.S. PATENT DOCUMENTS 9,795,451 B2    10/2017    Gorek et al.
2012/0172700 A1    7/2012    Krishnan et al.
(Continued)

FOREIGN PATENT DOCUMENTS

WO    2017004482 A1    1/2017
WO    2021077081 A1    4/2021

OTHER PUBLICATIONS

Fritz, J., et al.: "Augmented Reality Visualization With Image Overlay for MRI-Guided Intervention: Accuracy for Lumbar Spinal Procedures With a 1.5-T MRI System", American Journal of Roentgenology, vol. 198, No. 3, Mar. 1, 2012 (Mar. 1, 2012), pp. W266-W273, XP055766666, US ISSN: 0361-803X, DOI: 10.2214/AJR.11.6918.
(Continued)

*Primary Examiner* — Rochelle D Turchen

(74) *Attorney, Agent, or Firm* — Quarles & Brady LLP

(57) ABSTRACT

Image-guided navigation for spinal cord treatments and therapies are described. The image-guided navigation is augmented with anatomical measurement data related to spinal cord and vertebral anatomy. From these data and medical image data, an augmented model of spinal cord anatomy is generated and/or navigation data can be generated for localizing spinal cord structures, such as by map-
(Continued)

ping the anatomical measurement data to the medical image data. The augmented model data and/or navigation data can be used for surgical navigation, stimulation parameter setting, electrode configuration selection, pre-surgical planning, surgical visualization, and so on.

32 Claims, 11 Drawing Sheets

(51) Int. Cl.
*A61B 34/00* (2016.01)
*A61B 34/10* (2016.01)
*A61B 90/00* (2016.01)

(52) U.S. Cl.
CPC ........ *A61B 90/37* (2016.02); *A61B 2034/105* (2016.02); *A61B 2034/107* (2016.02); *A61B 2034/108* (2016.02); *A61B 2034/2065* (2016.02)

(58) Field of Classification Search
CPC ........ A61B 2034/105; A61B 2034/107; A61B 2034/108; A61B 2034/2065
See application file for complete search history.

(56) References Cited

U.S. PATENT DOCUMENTS

| | | | | |
|---|---|---|---|---|
| 2018/0301213 | A1* | 10/2018 | Zehavi | ...................... G06T 7/73 |
| 2018/0303552 | A1 | 10/2018 | Ryan et al. | |
| 2019/0146458 | A1 | 5/2019 | Roh et al. | |
| 2019/0149797 | A1* | 5/2019 | Casas | ................... H04N 13/156 |
| | | | | 348/47 |
| 2019/0262609 | A1* | 8/2019 | Brill | ................... A61N 1/36071 |

OTHER PUBLICATIONS

Mendez, I., et al.: "One Sentence Summary". bioRxiv, Feb. 2, 2020 (Feb. 2, 2020), XP055765733, DOI: 10.1101/2020.01.31.928804 Retrieved from the Internet: URL:https://www.researchgate.net/profile/1 gor Lavrov3/publication/338997304 Segment•specific orientation of the dorsal and ventral roots for precise therapeutic-targeting of human spinal cord/links/5ea6d04f299b f112561295f1/Segment-specific-orientation•of-the-dorsal-and-ventral-roots-for-precise-therapeu.
International Search Report of related PCT/US2020/056319, mailed on Jan. 27, 2021, 3 pages.
Written Opinion of related PCT/US2020/056319, mailed on Jan. 27, 2021, 7 pages.

* cited by examiner

702

Navigation Platform

Patient during implantation

Spinal cord anatomical targets

802   Presurgical MRI to establish landmarks and relative dimensions

804   Patient in surgery

806   Surgical imaging using C-arm

808   Match vertebral landmarks using C-arm

810   Plan surgical targets and entry zones

812   Calculate distance to target relative to surgical entry

814   Place lead at determined location

816   Confirm lead location using C-arm

IMAGE-GUIDED NAVIGATION SYSTEM FOR TARGETED DELIVERY OF SPINAL CORD THERAPIES

CROSS-REFERENCE TO RELATED APPLICATIONS

This application represents the national stage entry of PCT/US2020/056319 filed on Oct. 19, 2020 and claims the benefit of U.S. Provisional Patent Application Ser. No. 62/916,640, filed on Oct. 17, 2019, and entitled "IMAGE-GUIDED AUGMENTED HYBRID NAVIGATION SYSTEM FOR TARGETED DELIVERY OF SPINAL CORD THERAPIES," the contents of which is herein incorporated by reference in its entirety.

BACKGROUND

The understanding of spinal cord functional neuroanatomy is important for diagnosis, treatment, and management of multiple neurosurgical and neurological disorders, including chronic pain, movement disorders, and spinal cord injury. Currently, little to no information is available on segment-specific spinal cord structures, spinal roots orientation and other spinal cord structures or measurements. In addition, due to the thickness of the dura, these structures cannot be directly visualized with conventional imaging techniques; therefore, these structures are infeasible to target using these conventional imaging technologies.

Spinal cord stimulation ("SCS") including, epidural stimulation, dorsal column, spinal rootlet, and dorsal root ganglion ("DRG") stimulation are adjustable and effective non-opioid analgesic solutions with demonstrated efficacy. However, the delivery of SCS therapy is not evidence-driven due to the fact that surgeons and physicians do not have access to spinal cord anatomy, due to the limitation of current imaging methods available in the clinic, which cannot accurately image the spinal cord and its detailed anatomy.

Previous attempts at imaging spinal cord anatomy have focused on diffusion tensor imaging ("DTI") and combinations with other imaging methods; however, DTI scans are resource intensive and require longer scan times. In general, DTI is also not part of current clinical SCS pre-surgical assessments, which make its use not feasible for routine SCS applications.

SUMMARY OF THE DISCLOSURE

The present disclosure addresses the aforementioned drawbacks by providing a method for providing navigation to an anatomical region of a spinal cord. Anatomical measurement data are accessed with a computer system, where the anatomical measurement data indicate quantitative measurements of spinal cord anatomy. Medical image data are also accessed with the computer system, where the medical image data were obtained from a subject and depict at least a spinal cord of the subject and one or more vertebrae of the subject. Navigation data are generated from the anatomical measurement data and the medical image data using the computer system to map the anatomical measurement data to the medical image data relative to the one or more vertebrae depicted in the medical image data. The navigation data provide navigation to an anatomical region of the spinal cord. The navigation data can then be displayed to a user in order to provide navigation to the anatomical region.

It is another aspect of the present disclosure to provide a method for generating augmented spinal cord anatomy model data. Anatomical measurement data are accessed with a computer system. These anatomical measurement data indicate quantitative measurements and/or locations of spinal cord anatomy. Medical image data obtained from a subject are also accessed with the computer system. The medical image data depict at least a spinal cord of the subject and one or more vertebrae of the subject. Augmented spinal cord anatomy model data are then generated with the computer system by mapping the anatomical measurement data to the medical image data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 4A shows an example schematic representation of vertebral spine and spinal cord with measured parameters. Examples of dorsal segments correspond to cervical C4, C5, C6; thoracic T6, T7; and lumbar L1, L2 L3, segments are shown. FIG. 4B shows segment and DREZ length of cervical, thoracic, and lumbar segments (C2-L5). Note the similar trend in DREZ length (green line) and segment length at dorsal column entry (blue line), although, segment length was overall higher across all segments except for lower lumbar segments (L3-L5), where no intersegmental space was observed. Segment length at bone entry (orange line) demonstrates consistent increase across all segments. FIG. 4C shows inferior articular facet to caudal rootlet distance (light blue line), intervertebral foramen to rostral rootlet distance (purple line), and intervertebral foramen to caudal rootlet distance (red line), which show similar trends across all segments. Data represent mean+/−STD, n=9, One-way ANOVA followed by Kruskal-Wallis, ($*p<0.05$, $p<0.01$ & $*p<0.001$).

DETAILED DESCRIPTION

Figure 1:
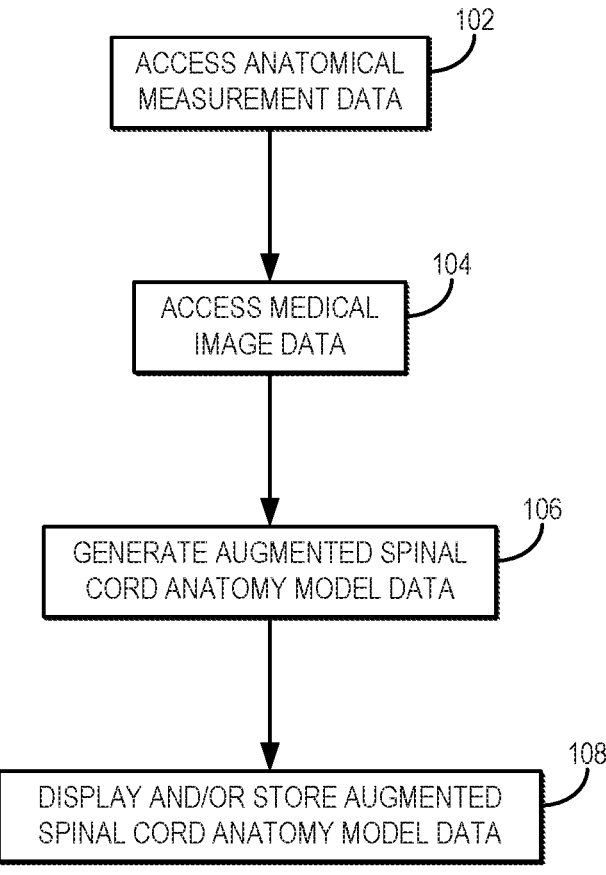
FIG. 1 is a flowchart setting forth the steps of an example method for generating augmented spinal cord anatomy data, and for using such data in a hybrid image-guided navigation system or other applications.

Described here are systems and methods for hybrid image-guided navigation for spinal cord treatments and therapies, in which the image-guided navigation is augmented with anatomical measurement data related to spinal cord and vertebral anatomy. The effectiveness of spinal cord stimulation ("SCS") for pain or spinal cord injury is impacted by precise targeting of stimulation.

The systems and methods described in the present disclosure overcome the limitations that different imaging modalities have in relation to accurately imaging spinal cord structures by combining an anatomical mapping algorithm with imaging data, which may be multimodal imaging data (e.g., CT scan, MRI, fluoroscopy, ultrasound). Such imaging data are generally obtained or otherwise available during pre-surgical assessment of patients undergoing spinal cord implants or other therapies or treatments The hybrid image-guided navigation described in the present disclosure can be utilized to predict or otherwise estimate spinal cord structures with reasonable accuracy with respect to vertebrae bony landmarks. These systems and methods can improve the accuracy of spinal cord therapies and treatments, including the placement of SCS implants, thereby obtaining better and more predictable clinical outcomes. In addition to SCS therapy, the hybrid image-guided navigation described in the present disclosure can enable the accurate administration of novel drugs and regenerative medicine to specific spinal cord areas for treatment of spinal cord injury, pain, stroke, Parkinson's disease, multiple sclerosis, and other neurodegenerative diseases.

In general, the systems and methods described in the present disclosure generate anatomically accurate augmented 2D or 3D models of the spinal cord (e.g., including spinal nerve, rootlet, tract) and vertebrae by combining patient-specific imaging data, which may be multimodal imaging data (e.g., CT, X-ray, MRI, fluoroscopy, ultrasound), with anatomical measurement data derived from anatomical relationships, or algorithms, that correlate bony landmarks with spinal cord structures.

These augmented models allow for predicting and visualizing spinal cord structures (e.g., spinal rootlets) that cannot be reliably tracked using only imaging modalities. In combination with spinal bony markers visualized in CT, X-ray, MRI, fluoroscopy, or ultrasound; electromyography ("EMG") signal data recorded from specific muscles; external landmarks (e.g., radio opaque markers, stationary device attachments); or combinations thereof, the augmented spinal cord model can allow for more accurate preplanning of therapy delivery methods and/or delivering therapies in a surgical setting. Therapies may include delivering SCS for chronic pain, spinal cord injury, Parkinson's disease, multiple sclerosis, or may include surgical procedures including rhizotomy, ablation, targeted drug delivery, stem cell injection, and other neurosurgery procedures that involve visualizing and targeting spinal cord structures or specific segments.

In some aspects, the systems and methods described in the present disclosure can be used to improve the localization and delivery of spinal cord therapies and treatments. For instance, optimal locations for delivering therapies or treatments can be identified, estimated, or otherwise determined. Additionally or alternatively, the systems and methods described in the present disclosure can also be implemented to adjust or otherwise determine one or more parameters about the therapies or treatments to be delivered. For instance, one or more electrical stimulation parameters can be estimated or adjusted. As another example, a selection of implanted electrodes to use in delivering a particular therapy or treatment can also be determined.

In some other aspects, the systems and methods described in the present disclosure can be used to improve the accuracy and safety of interventional procedures. For instance, anatomical locations in the spinal cord can be localized and tracked with greater accuracy using the systems and methods described in the present disclosure.

Referring now to FIG. 1, a flowchart is illustrated as setting forth the steps of an example method for generating augmented spinal cord anatomy model data and implementing such data for use in a hybrid image-guided navigation system.

The method includes accessing anatomical measurement data with a computer system, as indicated at step 102. The anatomical measurement data may be accessed, for instance, by retrieving such data from a memory, database, or other suitable data storage device or medium. The anatomical measurement data may include anatomical measurement data associated with the spinal cord, spinal cord structures, and/or vertebral bones. In some instances, the anatomical measurement data may be representative of a subject population or group. For instance, the anatomical measurement data may be representative of a group of subjects that share common demographic data (e.g., age-matched, sex-matched), clinical data (e.g., similar disease states or conditions), or the like.

As one non-limiting example, the anatomical measurement data are representative of measured properties and parameters of spinal cord structures, and may include measurements of orientation angles, distances between structures, dimensions (e.g., length, width, diameter) of structures, numbers of structures, and so on. Examples include rostral rootlet angle, caudal rootlet angle, number of rootlets, width across columns, root diameter, transverse diameter, rostral rootlet to caudal rootlet length, segment length at dorsal column entry, segment length at bone entry, inferior articular facet to caudal rootlet distance, intervertebral foramen to rostral rootlet distance, and intervertebral foramen to caudal rootlet distance, and the like.

The anatomical measurement data may also include data associated with vertebral bones, or relating spinal cord structures to the vertebral bones. For instance, the anatomical measurement data may also include measurements of distances between structures, dimensions (e.g., length, width, diameter) of structures, and so on. Examples include mid-vertebral foramen length, vertebral bone length, intervertebral foramen distance, intervertebral foramen diameter, and so on.

The anatomical measurement data may include measurements or other data corresponding to the relationship between the spine and spinal cord segments. Such relationship data can be determined, for instance, based on a linear regression. As a non-limiting example, the following spine variables can be correlated with the intervertebral foramen to rostral and caudal rootlet distance: mid-vertebra foramen length, vertebral bone length, and intervertebral foramen distance. The highest correlation coefficient can then be used to determine a proper intersegmental vertebrae landmark and spine segment. These can be used as a reference to establish ratios between spine and spinal cord across segments. The means of the intersegmental landmark lengths (spine and spinal cord) can be used to obtain the ratios.

The method also includes accessing medical image data for a subject using the computer system, as indicated at step 104. Accessing the medical image data can include retrieving such data from a memory, database, or other suitable data storage device or medium. In other instances, accessing the medical image data can include acquiring such data with one or more medical imaging systems and communicating or otherwise transferring that data to a computer system, which may form a part of the one or more medical imaging systems. The medical image data can include one or more images acquired using a magnetic resonance imaging ("MRI") system; an x-ray system, including a digital radiography system, a fluoroscopy system, a computed tomography ("CT") system, and so on; a nuclear medicine system, such as a positron emission tomography ("PET") system, a single-photon emission computed tomography ("SPECT") system, and so on; an ultrasound system; an optical imaging system, such as an optical coherence tomography ("OCT") system; other suitable medical imaging systems; and combinations thereof.

Figure 2:
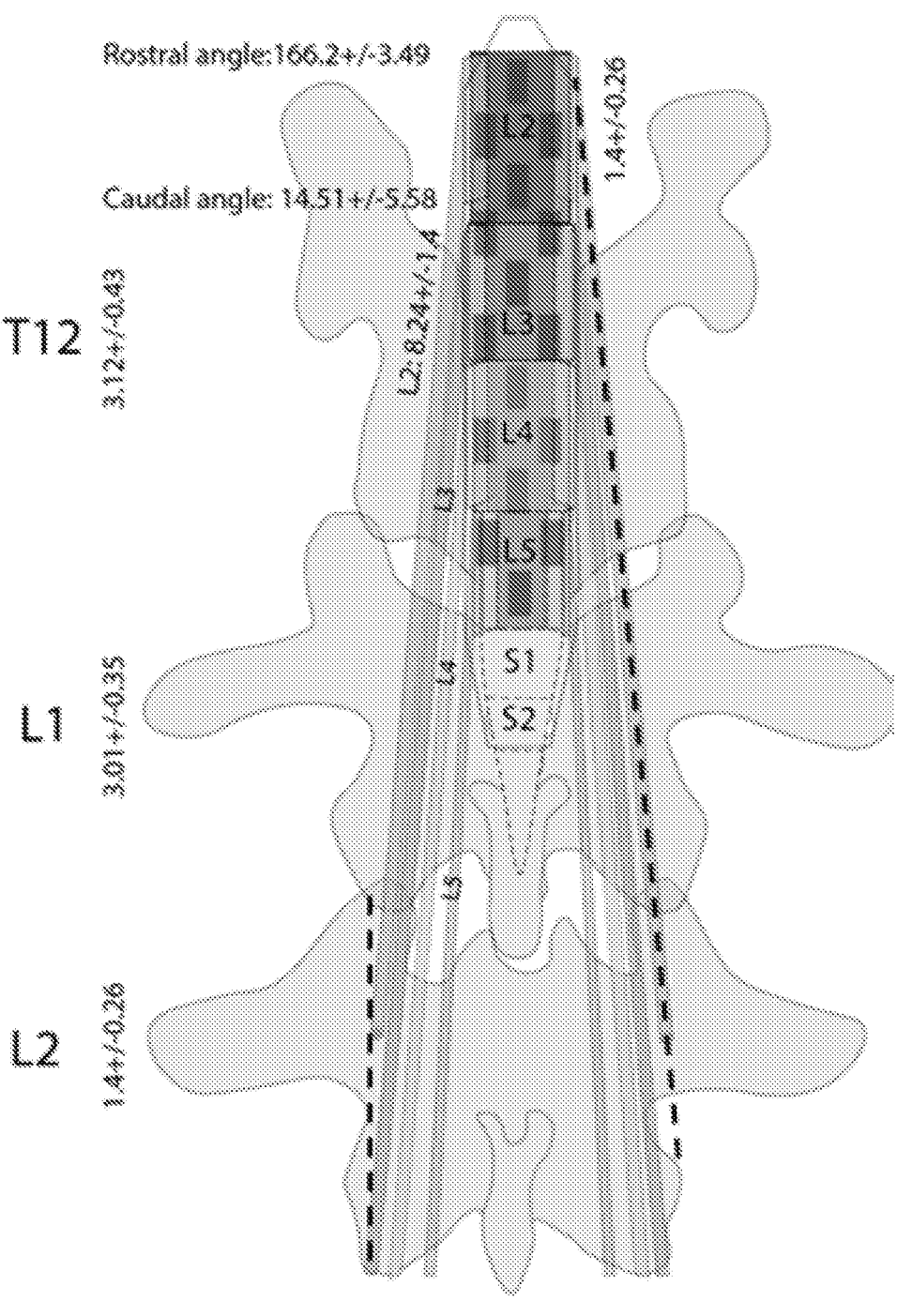
FIG. 2 shows an example diagram of vertebrae (T12-L2) and corresponding spinal cord segments (L2-S2) with array locations based on segment mapping.

Examples of anatomical measurement data and how they can be determined or generated are shown in FIGS. 2-5. FIG. 2 shows an example diagram of vertebrae (T12-L2) and corresponding spinal cord segments (L2-S2) with array locations based on segment mapping.

Figure 3:
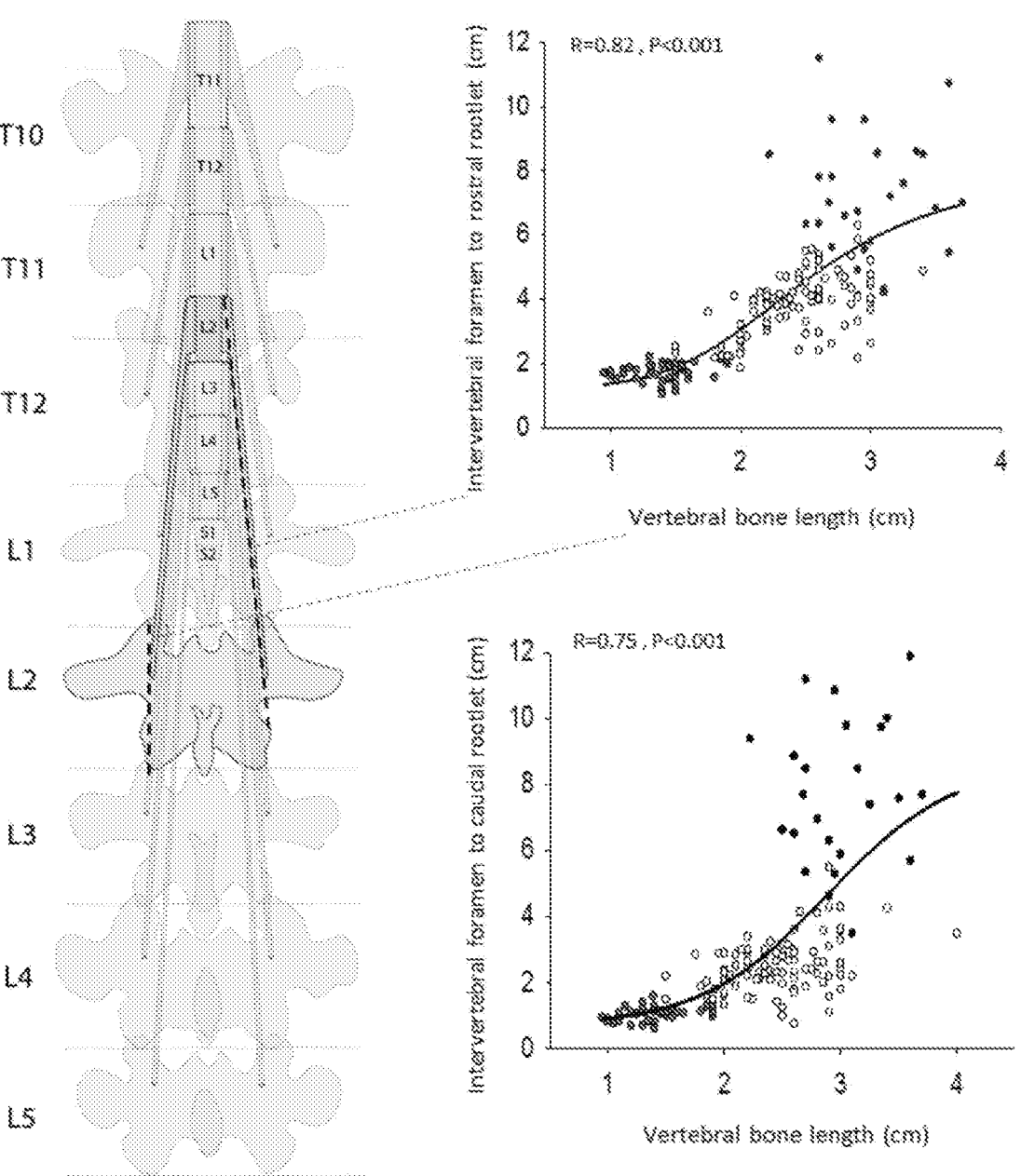
FIG. 3 shows an example diagram of vertebrae (T10-L5) and corresponding spinal cord segments (T11-S2); dotted lines mark L2 intervertebral foramen to rostral rootlet distance and vertebral bone size. A scatter plot of vertebral bone length versus intervertebral foramen to rostral rootlet distance is also shown. In this plot, Spearman coefficient of correlation value was found to be 0.82 with $P<0.001$. The equation used to fit the curve was, $f=8.5/(1+\exp(-(x-2.4)/0.75))$. A scatter plot of vertebral bone length versus intervertebral foramen to caudal rootlet distance is also shown. In this plot, Spearman coefficient of correlation value was found to be 0.75 with $P<0.001$. The equation used to fit the curve was, $f=7.5/(1+\exp(-(x-2.88)/0.54))$.

FIG. 3 shows an example diagram of vertebrae (T10-L5) and corresponding spinal cord segments (T11-52); dotted lines mark L2 intervertebral foramen to rostral rootlet distance and vertebral bone size. A scatter plot of vertebral bone length versus intervertebral foramen to rostral rootlet distance is also shown. In this plot, Spearman coefficient of correlation value was found to be 0.82 with P<0.001. The equation used to fit the curve was, $f=8.5/(1+\exp(-(x-2.4)/0.75))$. A scatter plot of vertebral bone length versus intervertebral foramen to caudal rootlet distance is also shown. In this plot, Spearman coefficient of correlation value was found to be 0.75 with P<0.001. The equation used to fit the curve was, $f=7.5/(1+\exp(-(x-2.88)/0.54))$.

Figure 4A:
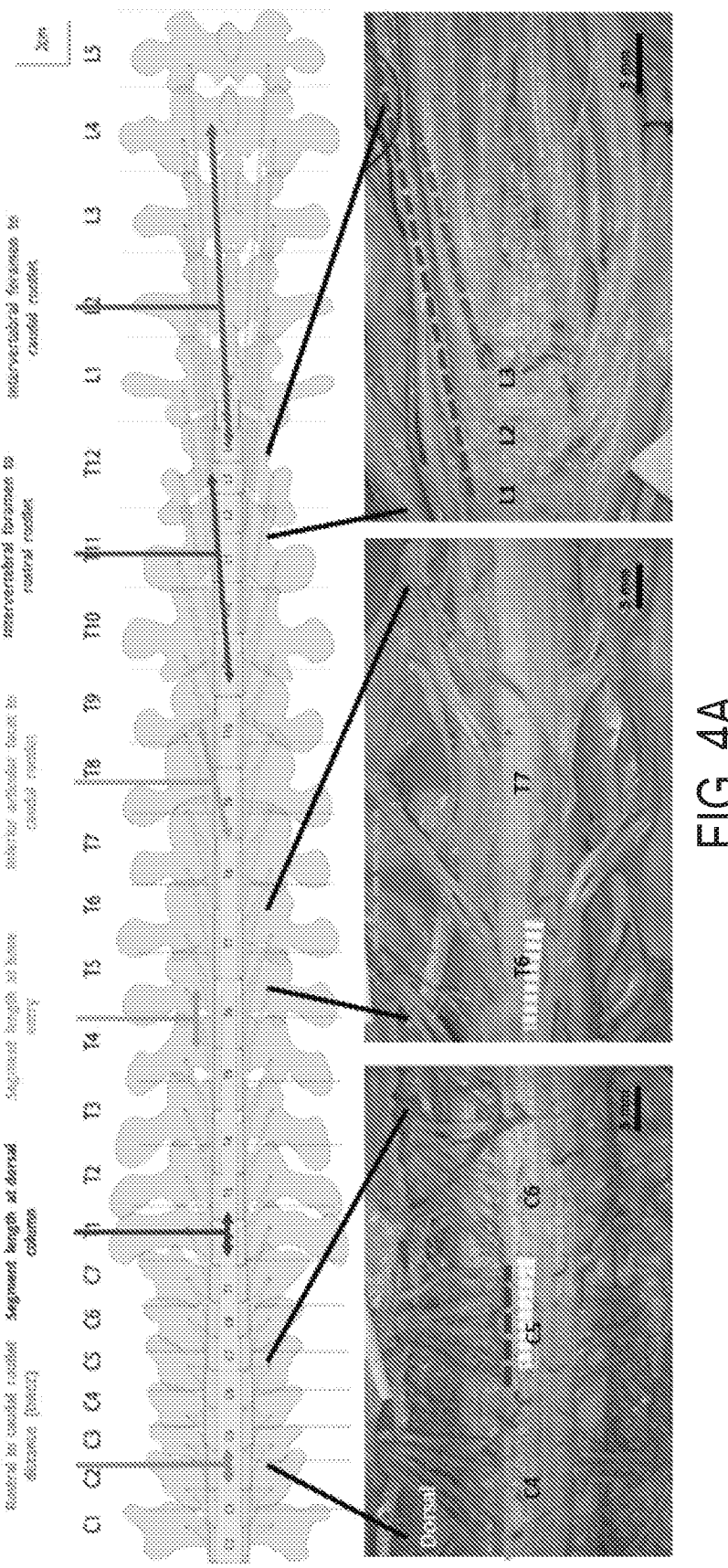
FIGS. 4A-4C show spinal cord anatomic parameters and measurements results.
Figures 4B, 4C:
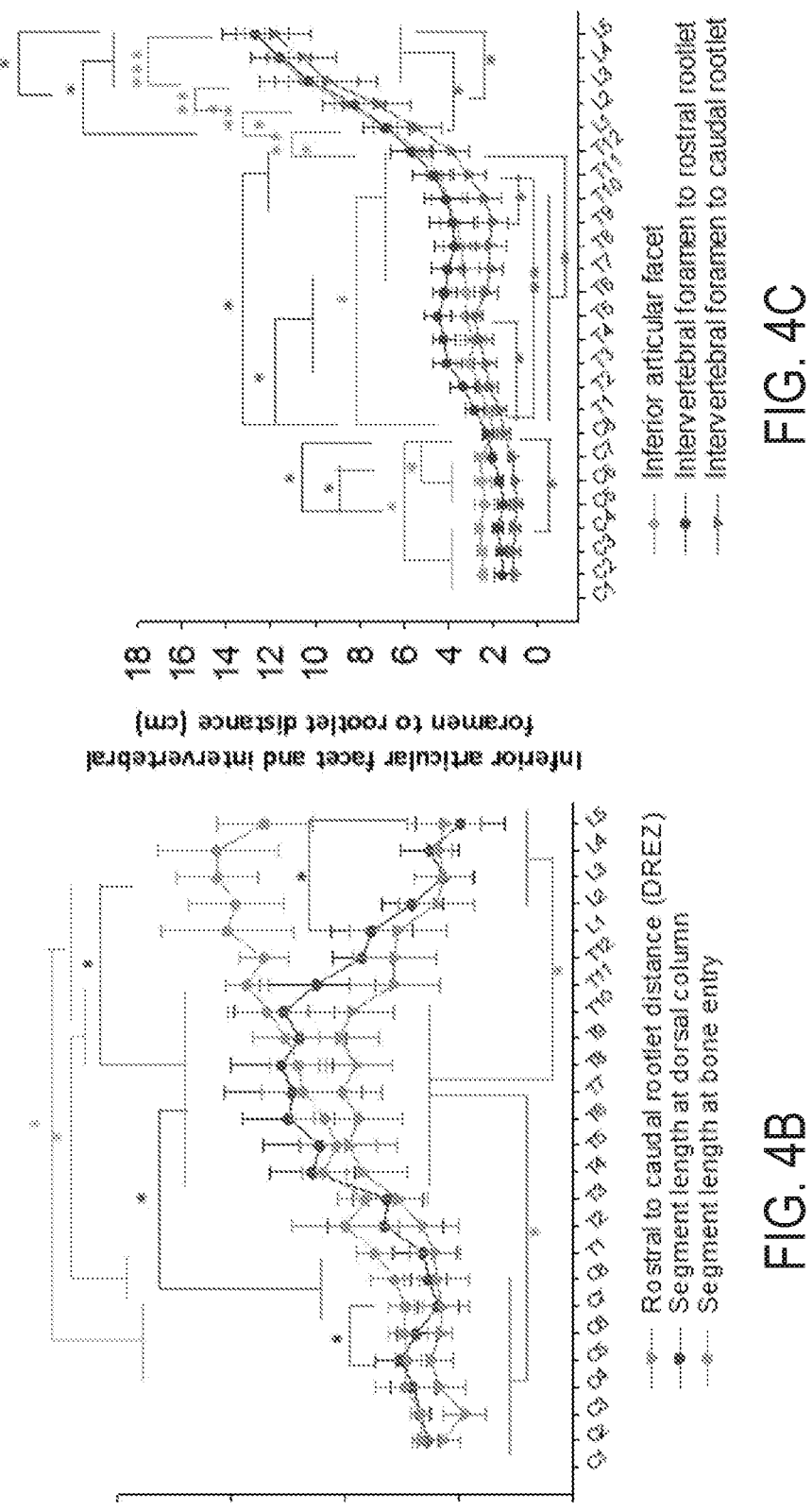

FIGS. 4A-4C show spinal cord anatomic parameters and measurements results. FIG. 4A shows an example schematic representation of vertebral spine and spinal cord with measured parameters. Examples of dorsal segments correspond to cervical C4, C5, C6; thoracic T6, T7; and lumbar L1, L2 L3, segments are shown. FIG. 4B shows segment and DREZ length of cervical, thoracic, and lumbar segments (C2-L5). Note the similar trend in DREZ length (green line) and segment length at dorsal column entry (blue line), although, segment length was overall higher across all segments except for lower lumbar segments (L3-L5), where no intersegmental space was observed. Segment length at bone entry (orange line) demonstrates consistent increase across all segments. FIG. 4C shows inferior articular facet to caudal rootlet distance (light blue line), intervertebral foramen to rostral rootlet distance (purple line), and intervertebral foramen to caudal rootlet distance (red line), which show similar trends across all segments. Data represent mean+/−STD, n=9, One-way ANOVA followed by Kruskal-Wallis, (*p<0.05, p<0.01 & *p<0.001).

Figure 5:
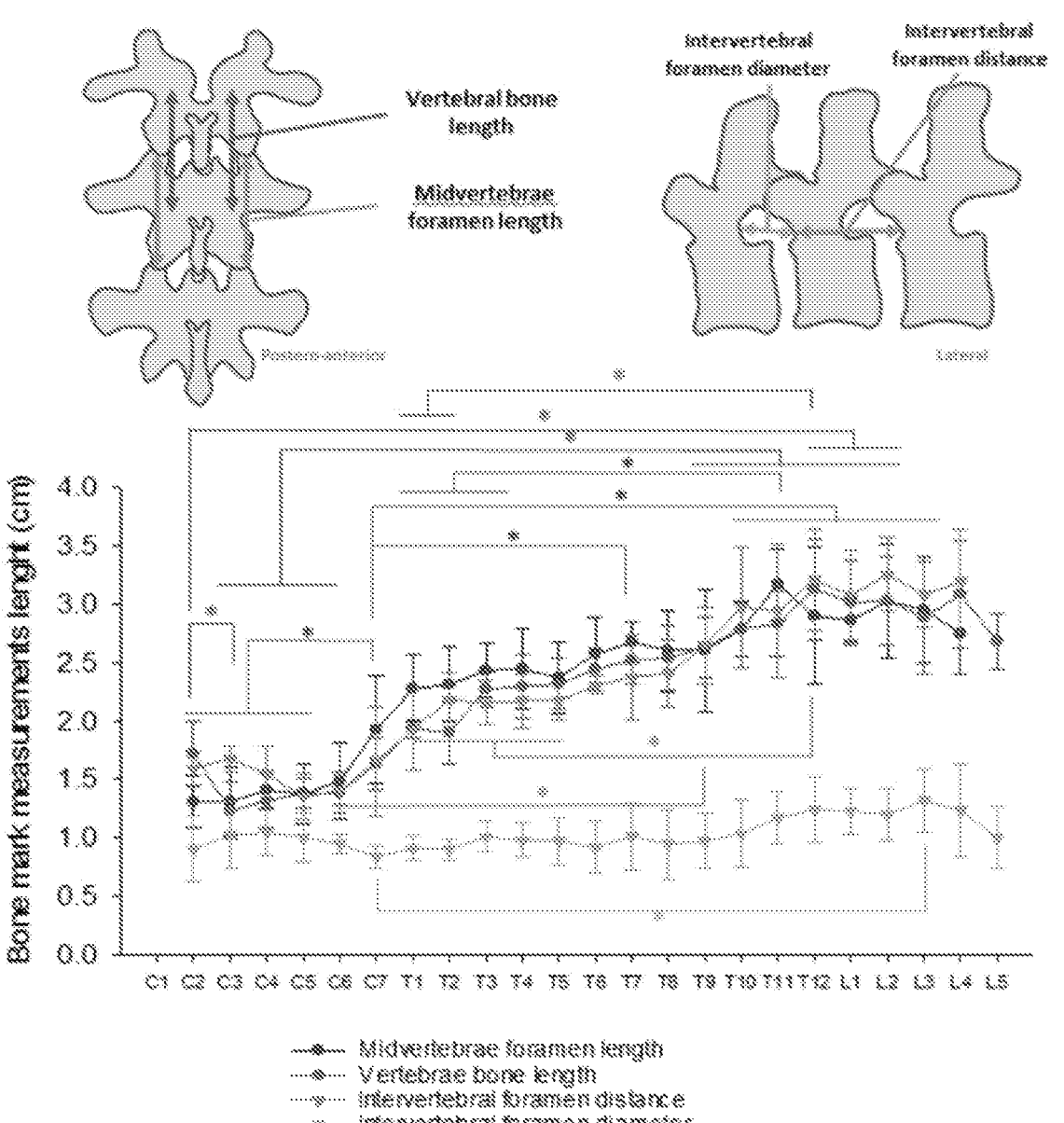
FIG. 5 shows vertebral spinal anatomic landmarks and results. The upper portion of FIG. 5 shows spine anatomic landmarks (postero-anterior and lateral view). The lower portion of FIG. 5 shows mid-vertebrae foramen length (blue line), vertebral bone length (red line), intervertebral foramen distance (green line) and intervertebral foramen diameter (orange line) for C2-L5. Note the trend equivalence in mid-vertebrae foramen length, vertebrae bone length, and intervertebral foramen distances as intervertebral measurements and vertebral size increase towards lower levels in a gradual pattern. T12 vertebra had the highest length size, as well as the highest mid-vertebrae foramen distance (T11-T12), and intervertebral foramen distance (T12-L1). (Data represent mean+/–STD, n=9, One-way ANOVA followed by Kruskalwalis, *p<0.05, p<0.01 &*p<0.001).

FIG. 5 shows vertebral spinal anatomic landmarks and results. The upper portion of FIG. 5 shows spine anatomic landmarks (postero-anterior and lateral view). The lower portion of FIG. 5 shows mid-vertebrae foramen length (blue line), vertebral bone length (red line), intervertebral foramen distance (green line) and intervertebral foramen diameter (orange line) for C2-L5. Note the trend equivalence in mid-vertebral foramen length, vertebrae bone length, and intervertebral foramen distances as intervertebral measurements and vertebral size increase towards lower levels in a gradual pattern. T12 vertebra had the highest length size, as well as the highest mid-vertebrae foramen distance (T11-T12), and intervertebral foramen distance (T12-L1). (Data represent mean+/−STD, n=9, One-way ANOVA followed by Kruskalwalis, *p<0.05, p<0.01 &*p<0.001).

Using the anatomical measurement data and the medical image data, augmented spinal cord anatomy model data are generated with the computer system, as indicated at step 106. As an example, the augmented spinal cord anatomy model data can be generated based in part on an anatomical mapping of the anatomical measurement data to one or more of the images contained in the medical image data. In some instances, the anatomical measurement data can be mapped to one or more medical images using a machine learning or artificial intelligence algorithm that has been trained to map between anatomical measurement data and medical images. As one non-limiting example, an image can be input to a suitably trained machine learning algorithm, generating output as augmented spinal cord anatomy model data, which may include location outputs with respect to vertebrae. Such machine learning algorithms may include artificial neural networks (e.g., convolutional neural networks, residual neural networks, and so on) in addition to other suitable machine learning algorithms.

The augmented spinal cord anatomy model data can then be stored for later use, displayed to a user, or otherwise used as described in the present disclosure to provide for hybrid image-guided navigation in spinal cord therapies and treatments, as indicated at step 108. The augmented spinal cord anatomy data may in some instances be displayed to a user be generated one or more display elements based on the augmented spinal cord anatomy data and displaying those display elements on a monitor or other suitable display. In some instances, these display elements may be overlaid on other images, such as images contained in the medical image data. The augmented spinal cord anatomy data may also be displayed as part of, or in conjunction with, a graphical user interface ("GUI") that may enable a user to interact with the augmented spinal cord anatomy data. Example uses and applications of such augmented spinal cord anatomy data are described in detail below.

Example Implementations—Electrode Placement and Optimization

Determining Optimal Stimulation Location(s)

As noted above, in one aspect, the systems and methods described in the present disclosure can be implemented to accurately place spinal leads, or an array, at a desired location. As one example, if the location of chronic pain is known for a particular subject, the navigation system can generate a suggestion for an optimum location for the placement of a stimulating lead or array before trial stimulation within the augmented model. Similarly, such locations can be determined for other treatments or therapies in conditions other than chronic pain. This can significantly reduce the trial stimulation period. The subject-specific augmented model can store data about the location of the trial lead or array, optimum stimulation parameters for pain relief, electrodes to be used for pain relief, and can therefore make permanent lead or array placement more efficient. In some instances, by providing accurate locations in the spinal cord that need to be targeted, the navigation system can eliminate the requirement of trial stimulation or can significantly reduce the time and complexity of trial stimulation. Following insertion of the lead or array the system can provide electrode selection and/or stimulation parameter suggestion, thereby significantly reducing post-surgical effort to determine best parameters for the patient for pain relief.

Optimal Electrode Placement and Selection

In another aspect, the systems and methods described in the present disclosure can be implemented to optimize the selection of stimulation electrodes to use when applying electrical stimulation to a subject. Additionally or alternatively, the systems and methods described in the present disclosure can be implemented to optimize stimulation parameters for use with controlling an SCS system to generate electrical stimulation.

For SCS applications, the augmented system can suggest electrode, electrode pairs, or combinations of electrodes or voltage/current settings for generating electrical stimulation fields or orienting electric fields for the segment specific angle of dorsal and ventral spinal cord. This allows optimum and selective stimulation of spinal cord at minimum threshold thereby reducing spinal cord damage due to overstimulation, improving battery longevity and improve therapeutic outcome.

In addition, for spinal cord stimulation applications with spinal leads or arrays spanning multiple segments, the augmented spinal cord anatomy data can be analyzed to suggest optimum locations for inserting the lead or array. Moreover, these suggestions can be informed based on a user selection of the type of lead or array, manufacturer, and/or model. In some other instances, the system may be able to provide the user with a suggested selection based on an analysis of the augmented spinal cord anatomy data. For example, in spinal lead implant for pain applications, the system can provide an optimum location to make an incision, or an optimum location to insert the percutaneous needle. The system can also use the augmented spinal cord anatomy data to generate a display that depicts optical or other visible marks overlaid on the patient medical image data to assist the physician or operator.

Upon insertion based on the subject-specific augmented model, the system can also suggest electrode, electrode pairs, or combinations of electrodes or voltage, current, or other stimulation parameters (e.g., frequency, pulse width) for generating electrical fields that target specific spinal segments or spinal cord anatomy for effective blocking or activation for the specific application.

Designing Anatomy-Specific Electrodes

The anatomy-specific augmented model and/or underlying anatomical measurements can also guide the design and/or fabrication of custom leads or arrays for specific application to target spinal segment, rootlets, or other anatomy. In this way, the anatomy-specific electrode leads or arrays can be customized to obtain an optimal outcome for the stimulation delivered to that patient. The augmented model and/or underlying anatomical measurements can work in combination with a 3D printer or fabricator to develop custom arrays for the specific application and/or specific patient. For instance, the augmented spinal cord anatomy model can be processed to generate fabrication instructions for a 3D printer or other additive manufacturing system.

Accounting for Dynamic Motion or Tasks

The subject specific augmented model can also be combined with dynamic motion data or tasks (e.g., gait, specific task, breathing, body position, posture) to predict spinal rootlet or spinal cord shape, geometry, and location for the specific task. This can provide guidance for optimizing stimulation parameters for dynamic situations, thereby improving therapeutic outcome for the specific condition (e.g., pain, spinal cord injury, stroke, Parkinson's disease, multiple sclerosis, etc.).

Use in Closed Loop Systems

The subject specific augmented model, with or without a navigation system, can provide stereotactic data for targeting specific spinal cord segments or anatomy noninvasively. The augmented system can in some instances be combined with finite element models and/or electromyography recording systems in order to develop closed loop systems for optimum output for the specific therapy.

Accounting for Body Positioning and Movement

As still another example application of the systems and methods described in the present disclosure, the medical image data can be acquired with the patient in supine, prone, or other body position. The navigation system can apply an internal posture correction algorithm to match with the patient's body position on the surgical table. The internal algorithm of the navigation system might be guided by fluoroscopy, x-ray, or other imaging method used in the surgical suite. The navigation system can also take user's input to provide the best view for the surgeon.

Despite significant improvement with the anchoring technology implanted devices, spinal leads are still prone to migration. The navigation system can provide suggestions to the surgeon to account for such migration. In addition, spinal leads are likely to make different level of contacts with spinal cord based on the body position of the patient. The navigation system can provide implantation location guidance or stimulation parameter guidance to take that movement into account.

Example Implementations—Anatomy Visualization and Tracking

As another example application of the systems and methods described in the present disclosure, the navigation system can allow for predicting and visualizing spinal cord anatomy data, which may include the trajectory and entry of specific spinal cord rootlets into the dorsal column, spinal cord segment length, and intersegmental space based on the distance from that or any other vertebrae segment's bony landmarks. This spinal cord anatomy data, with or without visualization, can be used to navigate a manually guided, microdrive-guided, and/or robotically guided surgical tool or therapy delivery devices or needles into the epidural space, spinal canal, or inside the spinal cord.

The subject anatomy specific augmented model can also provide guidance for targeting ventral rootlets manually or by a robotic system. Upon establishing bony landmarks the system can predict ventral rootlet locations and geometry with reasonable accuracy, with our without multimodal imaging data.

The augmented model can also suggest location of inter-root and inter-rootlet anastomoses in order to activate or block those segments or perform targeted surgeries. Inter-root anastomoses are connections between spinal roots and are composed of myelinated fibers. Inter-rootlet anastomoses can include crotches or connections between rootlets. As a non-limiting example, rootlets posterior to dorsal ganglions may be identified as nerve bundles, and may be divided into sub-bundles and finally rootlets before they enter the spinal cord, which are connected by inter-rootlet anastomoses.

During orthopedic spinal surgery, the augmented spinal cord system can work with other navigation systems or tools in order to provide visual or other data to a surgeon, thereby mitigating accidentally hitting or damaging the spinal cord structures (e.g. spinal cord, rootlet etc.). Many of the spine surgery procedures involve inserting surgical tools very close to the spinal cord. The augmented spinal cord model can be used to pre-program robotic surgery tools or warn the operator about the proximity of the tool to the spinal cord, or other otherwise provide a visual depiction of the spinal cord anatomy relative to bony structures for surgical planning and guidance purposes.

Figure 6:
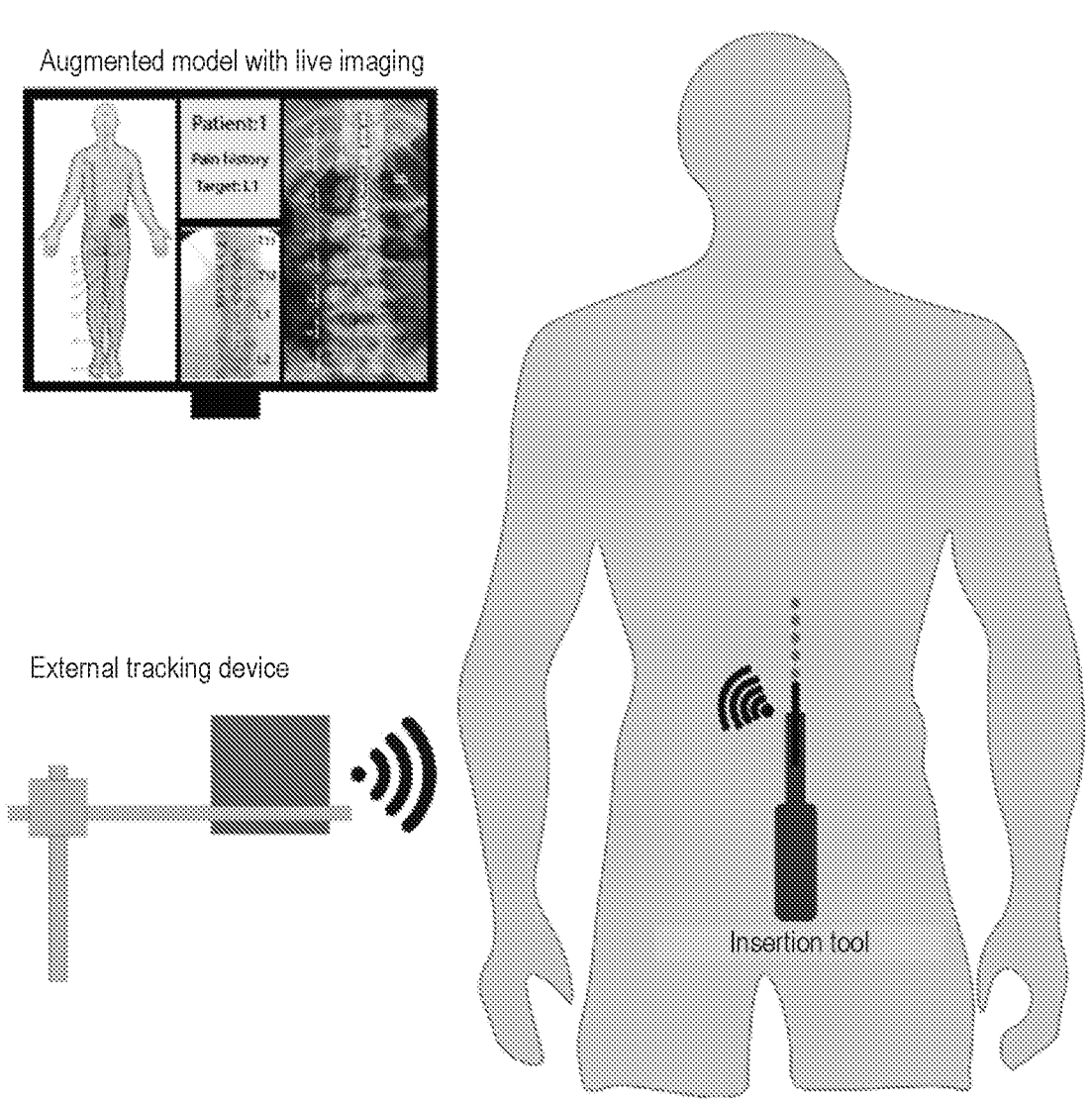
FIG. 6 shows an example of implementing an augmented model together with an external tracking device and robotic or manual insertion tool in a surgical or operating room setting.

As noted above, in some surgical settings, a subject specific augmented model can be combined with an external tracking system (e.g. electromagnetic signal based system, optical tracking system, inertial sensor based) to manually navigate surgical tools or place implantable devices (e.g., spinal lead, intraspinal electrode, needle) into specific regions of the spinal cord. The surgical tool might have active sensor or radiologically visible component that will communicate with external tracking system. The navigation system can provide real-time feedback to the operator about the location of the inserted lead or devices and make it visible in the augmented model. For example, the navigation system might warn the operator if the lead or surgical tool is about to hit or damage any spinal structures or accidentally enters the ventral region. Such feedback can be visual feedback, auditory feedback, and/or haptic feedback. An example of implementing an augmented model together with an external tracking device and robotic or manual insertion tool in a surgical or operating room setting is illustrated in FIG. 6.

Figure 7:
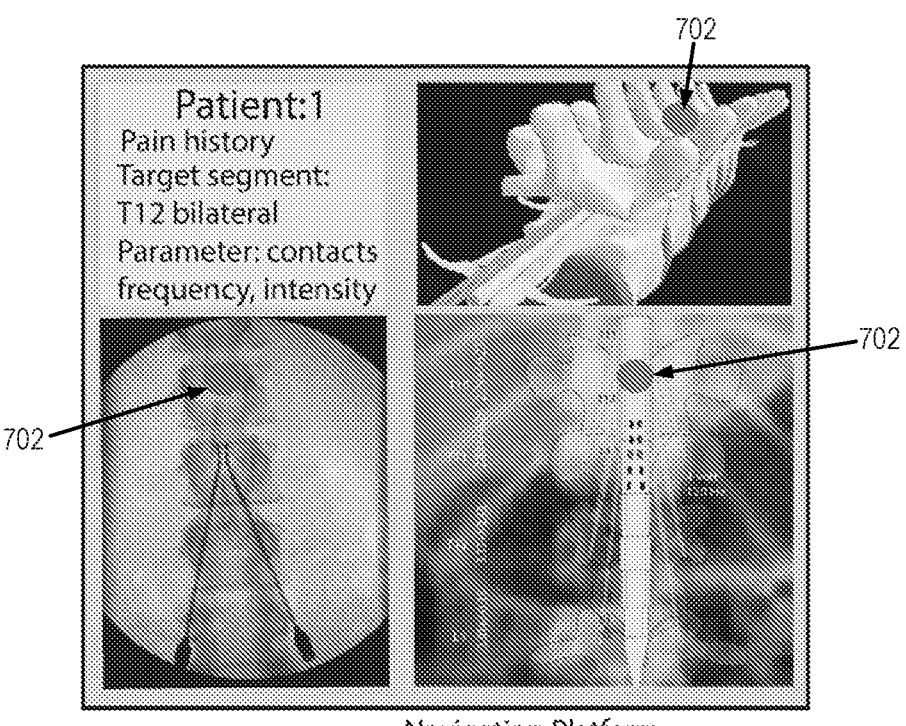
FIG. 7 shows an example of a navigation system implementation for providing navigation to an anatomical region of a spinal cord.
Figure 7:
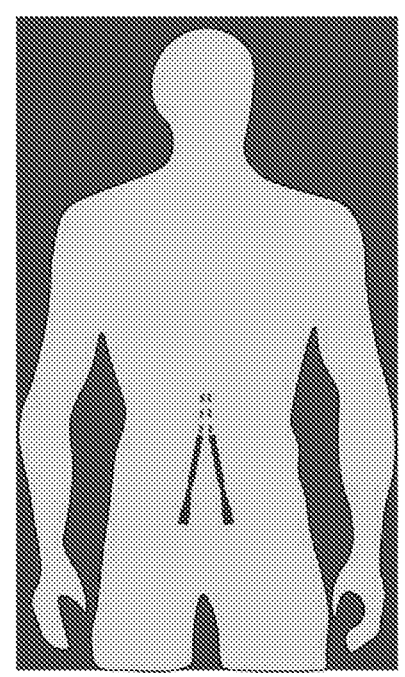
Figure 7:
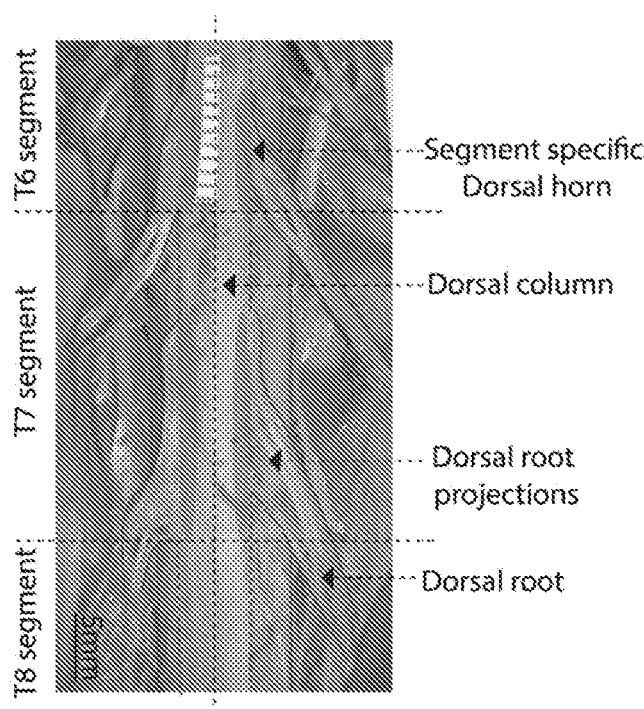

FIG. 7 shows a graphical representation of an example navigation system implemented during a spinal cord stimulation lead insertion procedure. The navigation system integrates pre-surgical patient imaging with the systems and methods described in the present disclosure in order to provide surgeons with a patient-specific detailed map of critical spinal cord structures and SCS targets. The red area 702 indicates potential targets of spinal cord stimulation. The navigation system provides reliable and repeatable targeting of approved neuromodulation leads during both trial and permanent implantation, including segment-specific targeting of dorsal column, dorsal horn, spinal roots, and other spinal cord anatomies. The navigation system can also provide guidance regarding therapy optimization, including contact selection, parameter optimization (e.g., intensity, frequency), and lead migration tracking.

The navigation system and augmented model can also work with a robotic insertion tool to navigate the surgical tools or implantable devices into a predetermined region of the spinal cord. The robotic navigation system can operate based on 2D or 3D coordinates generated by the augmented model.

The augmented spinal cord anatomy data can be implemented with a virtual reality system, an augmented reality system, or combinations thereof, in order to improve surgical planning for SCS implantation or other interventional procedures, or to assist with injecting drugs or other therapeutic agents with maximum accuracy.

Thus, in some aspects, the systems and methods described in the present disclosure can be implemented as a navigation system for delivering treatment and/or therapies to one or more specific anatomical regions of the spinal cord, as described above. Advantageously, such a navigation system is capable of localizing treatment regions in the spinal cord that otherwise cannot be reliably visualized with conventional imaging techniques. As described above, the navigation system can predict the location of spinal cord structures with respect to vertebrae and other bony landmarks. In this way, the navigation system can be advantageously be used during minimally invasive surgeries and/or therapy deliveries. The navigation system can implement an augmented spinal cord anatomy model, integrated tracking hardware, and/or live visualization.

Spinal cord anatomies that can be localized and/or targeted using the systems and methods described in the present disclosure include, but are not limited to, specific spinal cord segments (e.g., cervical, thoracic, and lumbar segments); spinal cord midline and lateral targeting; dorsal column targeting; dorsal horn targeting; dorsal root entry zone ("DREZ") targeting; inter-DREZ targeting; and/or dorsal rootlet targeting.

Therapies that can be delivered based on localization, tracking, and/or guidance provided by the navigation system can include, but are not limited to, guiding spinal cord stimulation leads and/or arrays, such as to a preside spinal cord anatomy for chronic pain and/or spinal cord injury; electrode placement for non-invasive stimulation of spinal cord regions; surgical procedures, such as minimally invasive surgeries, rhizotomy, drug delivery, cell delivery, and/or tissue resection; and pre-surgical planning, surgical guidance, and/or post-surgical tracking.

The navigation systems described in the present disclosure can thus provide accurate targeting of SCS leads to segment-specific spinal cord structures, including dorsal columns, spinal cord midline, dorsal horns, and dorsal nerve rootlet projections. This navigation system is patient-specific and can adjust targeting based on individual neuroimaging and guidance from a previously created atlas, which contains detailed critical substructures of the human cadaver spinal cord. The navigation system can improve the quantification and efficiency of implantation surgeries, making SCS outcomes more predictable, improving both trial-to-permanent conversion rates and long-term pain relief. Furthermore, this navigation system can allow providers to deliver effective SCS neuromodulation at lower costs and overcome the challenges of a tightening reimbursement outlook.

Example Implementation—Implantation Workflow

Figure 8:
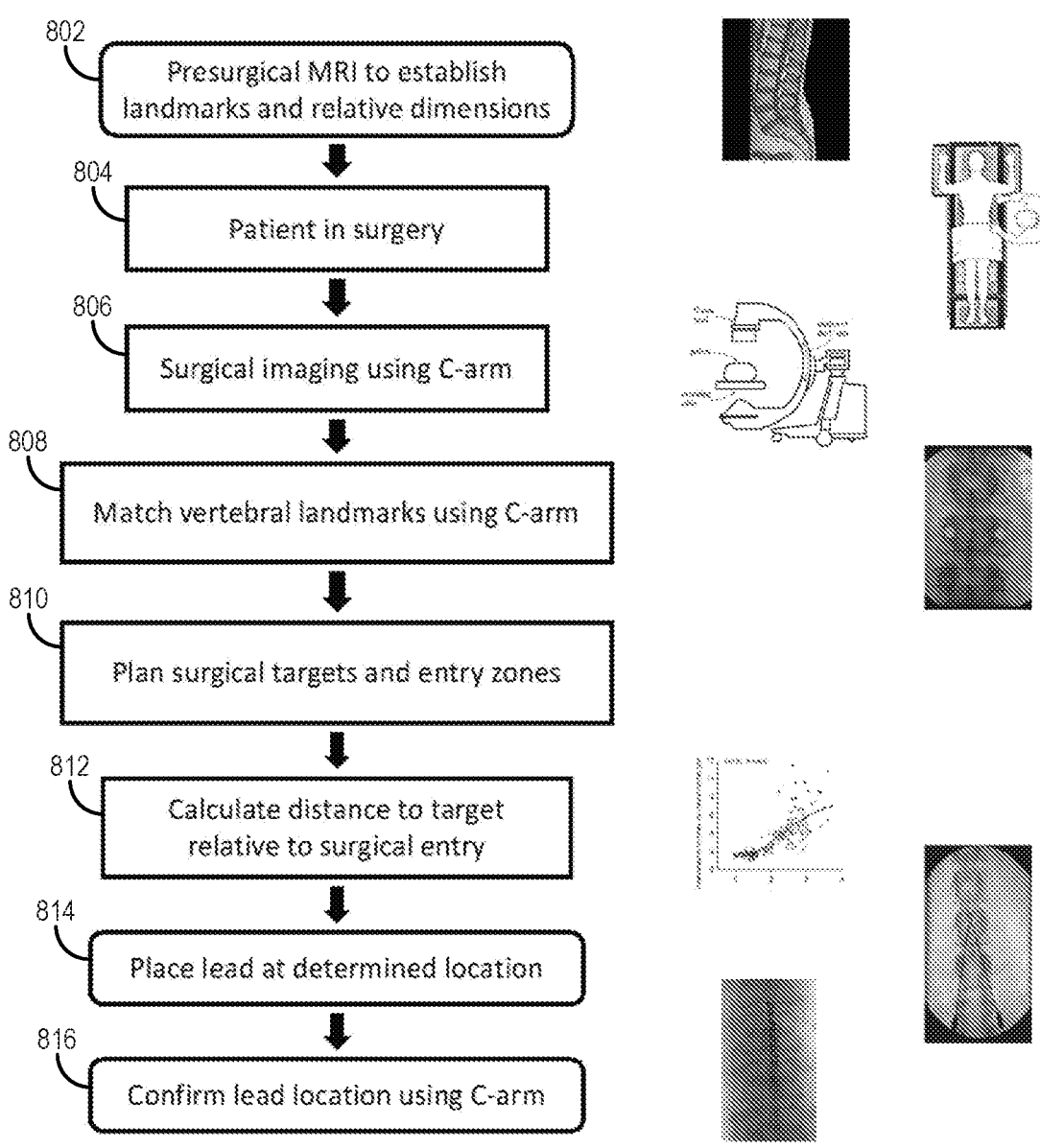
FIG. 8 shows an example spinal cord stimulation electrode implantation workflow that implements navigation systems in accordance with some embodiments described in the present disclosure.
Figure 9:
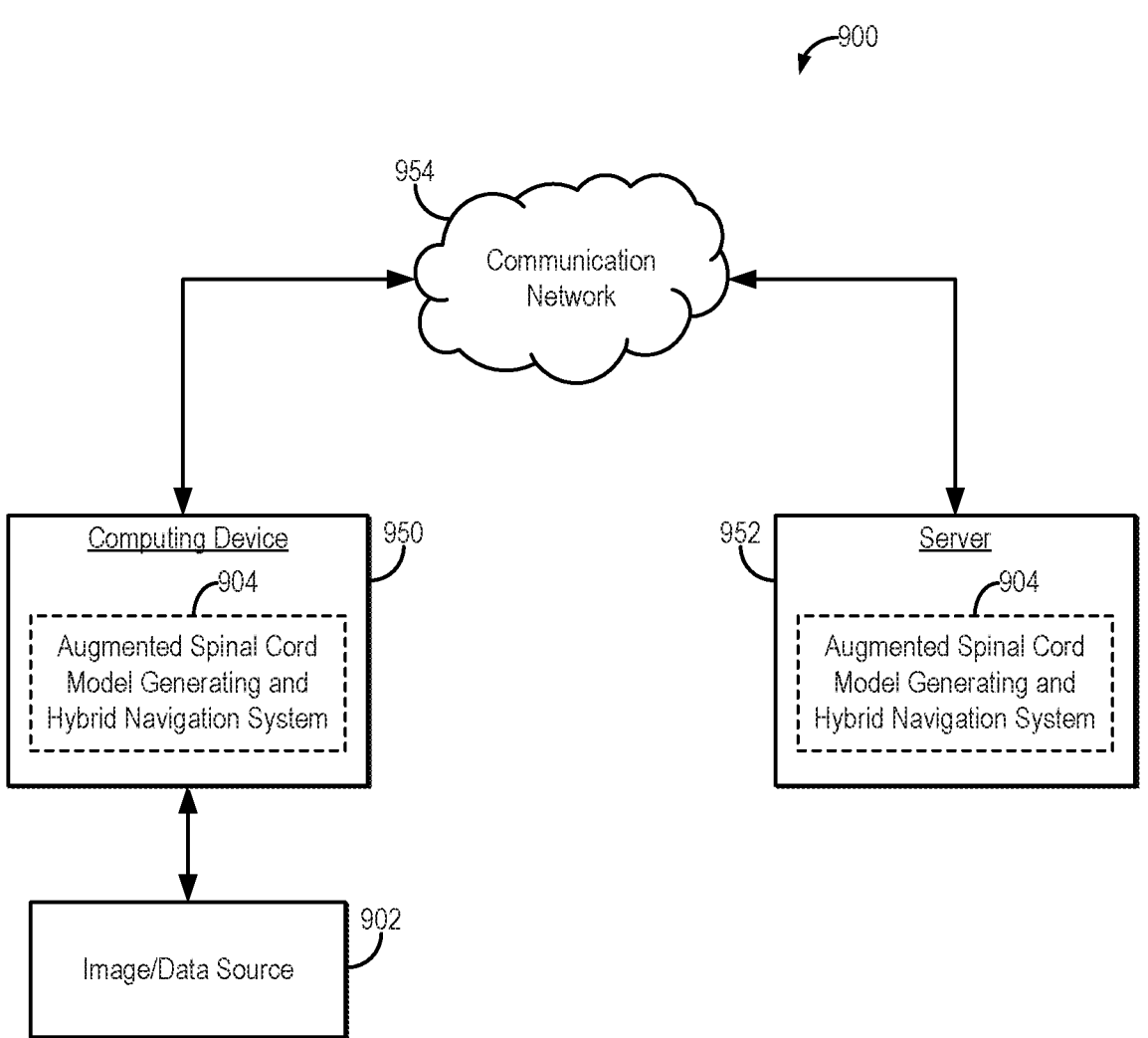
FIG. 9 is a block diagram of an example augmented spinal cord anatomy model generating and hybrid navigation system.
Figure 10:
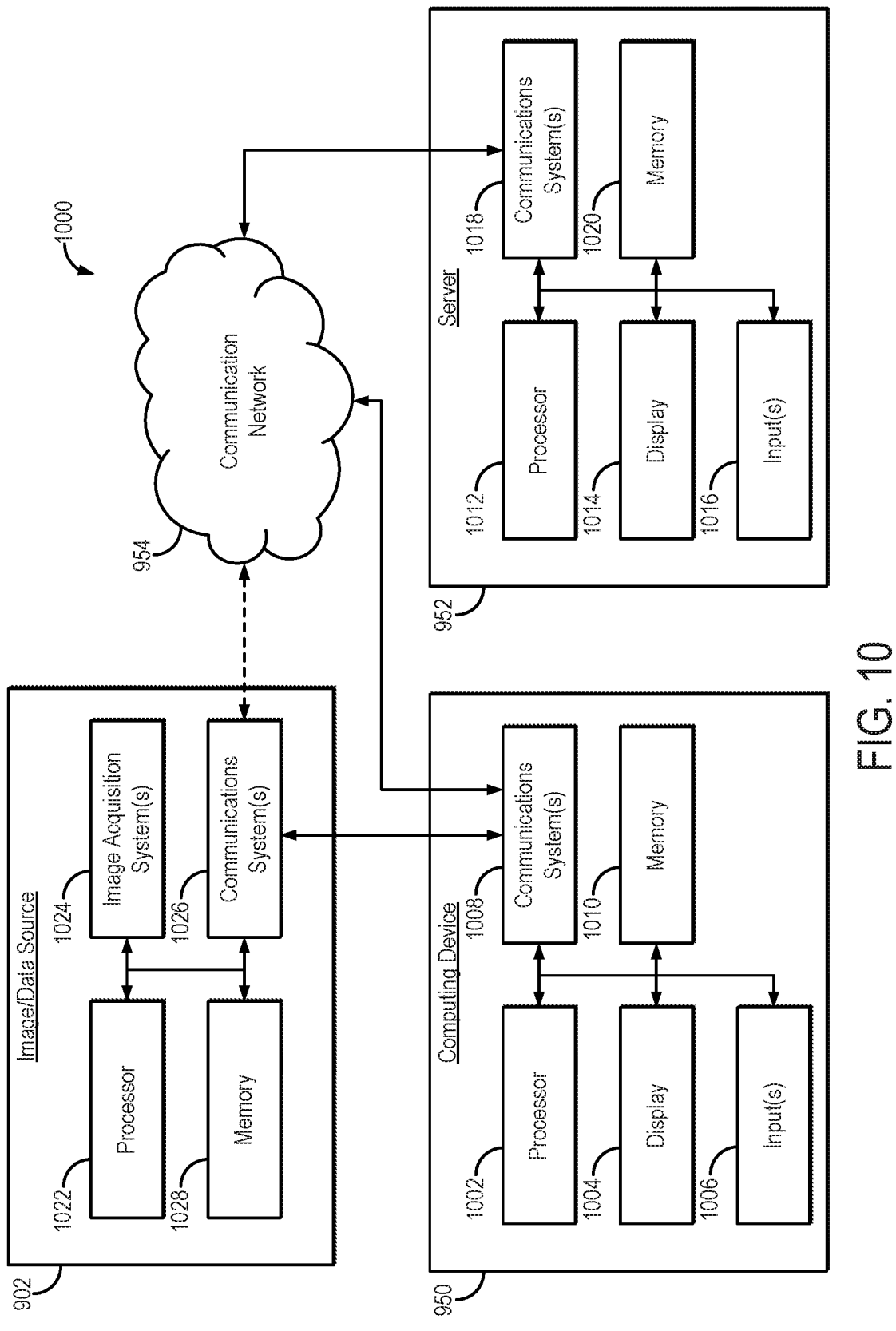
FIG. 10 is a block diagram of components that can implement the system of FIG. 9.

As one non-limiting example, the systems and methods described in the present disclosure can be used when implanting spinal cord stimulation electrode. An example workflow for such an implantation procedure is shown in FIG. 8. Patient-specific anatomy is utilized within a navigation system that implements the techniques described in the present disclosure in order to achieve accurate placement of SCS leads. This example implantation workflow can reduce the need for repeated C-arm imaging (as is currently used in surgery), thereby lowering the radiation dose to which the patient is exposed. Further, the implantation workflow can reduce surgical complexity and make implantation more efficient.

The workflow includes obtaining presurgical images using MRI in order to establish landmarks and relative dimensions, as indicated at step 802. The patient is the placed into surgery, as indicated at step 804. Surgical imaging of the patient is then performed, such as via C-arm x-ray imaging, as indicated at step 806. Bony landmarks, such as vertebral landmarks, are then matched using the C-arm images, as indicated at step 808. Surgical targets and entry zones are then planned, as indicated at step 810. The distance to each target relative to surgical entry is then calculated, as indicated at step 812. Using this information, the leads can be implanted at the determined locations, as indicated at step 814. The lead locations can then be confirmed via imaging, such as additional C-arm x-ray imaging, as indicated at step 816.

Example Systems

Referring now to FIG. 7, an example of a system 700 for generating augmented spinal cord anatomy model data and providing hybrid image-guided navigation in accordance with some embodiments of the systems and methods described in the present disclosure is shown. As shown in FIG. 7, a computing device 750 can receive one or more types of data (e.g., anatomical measurement data, medical image data) from image/data source 702, which may be a medical image/data source. In some embodiments, computing device 750 can execute at least a portion of an augmented spinal cord model generating and hybrid navigation system 704 to generate augmented spinal cord anatomy data from anatomical measurement data and medical image data received from the image/data source 702.

Additionally or alternatively, in some embodiments, the computing device 750 can communicate information about data received from the image/data source 702 to a server 752 over a communication network 754, which can execute at least a portion of the augmented spinal cord model generating and hybrid navigation system 704. In such embodiments, the server 752 can return information to the computing device 750 (and/or any other suitable computing device) indicative of an output of the augmented spinal cord model generating and hybrid navigation system 704.

In some embodiments, computing device 750 and/or server 752 can be any suitable computing device or combination of devices, such as a desktop computer, a laptop computer, a smartphone, a tablet computer, a wearable computer, a server computer, a virtual machine being executed by a physical computing device, and so on. The computing device 750 and/or server 752 can also reconstruct images from the data.

In some embodiments, image/data source 702 can be any suitable source of image data (e.g., measurement data, images reconstructed from measurement data), such as a medical imaging system, another computing device (e.g., a server storing image data), and so on. In some embodiments, image/data source 702 can be local to computing device 750. For example, image/data source 702 can be incorporated with computing device 750 (e.g., computing device 750 can be configured as part of a device for capturing, scanning, and/or storing images). As another example, image/data source 702 can be connected to computing device 750 by a cable, a direct wireless link, and so on. Additionally or alternatively, in some embodiments, image/data source 702 can be located locally and/or remotely from computing device 750, and can communicate data to computing device 750 (and/or server 752) via a communication network (e.g., communication network 754).

In some embodiments, communication network 754 can be any suitable communication network or combination of communication networks. For example, communication network 754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 754 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Referring now to FIG. 8, an example of hardware 800 that can be used to implement image/data source 702, computing device 750, and server 752 in accordance with some embodiments of the systems and methods described in the present disclosure is shown. As shown in FIG. 8, in some embodiments, computing device 750 can include a processor 802, a display 804, one or more inputs 806, one or more communication systems 808, and/or memory 810. In some embodiments, processor 802 can be any suitable hardware processor or combination of processors, such as a central processing unit ("CPU"), a graphics processing unit ("GPU"), and so on. In some embodiments, display 804 can include any suitable display devices, such as a computer monitor, a touchscreen, a television, and so on. In some embodiments, inputs 806 can include any suitable input devices and/or sensors that can be used to receive user input, such as a keyboard, a mouse, a touchscreen, a microphone, and so on.

In some embodiments, communications systems 808 can include any suitable hardware, firmware, and/or software for communicating information over communication network 754 and/or any other suitable communication networks. For example, communications systems 808 can include one or more transceivers, one or more communication chips and/or chip sets, and so on. In a more particular example, communications systems 808 can include hardware, firmware and/or software that can be used to establish a Wi-Fi connection, a Bluetooth connection, a cellular connection, an Ethernet connection, and so on.

In some embodiments, memory 810 can include any suitable storage device or devices that can be used to store instructions, values, data, or the like, that can be used, for example, by processor 802 to present content using display 804, to communicate with server 752 via communications system(s) 808, and so on. Memory 810 can include any suitable volatile memory, non-volatile memory, storage, or any suitable combination thereof. For example, memory 810 can include RAM, ROM, EEPROM, one or more flash drives, one or more hard disks, one or more solid state drives, one or more optical drives, and so on. In some embodiments, memory 810 can have encoded thereon, or otherwise stored therein, a computer program for controlling operation of computing device 750. In such embodiments, processor 802 can execute at least a portion of the computer program to present content (e.g., images, user interfaces, graphics, tables), receive content from server 752, transmit information to server 752, and so on.

In some embodiments, server 752 can include a processor 812, a display 814, one or more inputs 816, one or more communications systems 818, and/or memory 820. In some embodiments, processor 812 can be any suitable hardware processor or combination of processors, such as a CPU, a GPU, and so on. In some embodiments, display 814 can include any suitable display devices, such as a computer monitor, a touchscreen, a television, and so on. In some embodiments, inputs 816 can include any suitable input devices and/or sensors that can be used to receive user input, such as a keyboard, a mouse, a touchscreen, a microphone, and so on.

In some embodiments, communications systems 818 can include any suitable hardware, firmware, and/or software for communicating information over communication network 754 and/or any other suitable communication networks. For example, communications systems 818 can include one or more transceivers, one or more communication chips and/or chip sets, and so on. In a more particular example, communications systems 818 can include hardware, firmware and/or software that can be used to establish a Wi-Fi connection, a Bluetooth connection, a cellular connection, an Ethernet connection, and so on.

In some embodiments, memory 820 can include any suitable storage device or devices that can be used to store instructions, values, data, or the like, that can be used, for example, by processor 812 to present content using display 814, to communicate with one or more computing devices 750, and so on. Memory 820 can include any suitable volatile memory, non-volatile memory, storage, or any suitable combination thereof. For example, memory 820 can include RAM, ROM, EEPROM, one or more flash drives, one or more hard disks, one or more solid state drives, one or more optical drives, and so on. In some embodiments, memory 820 can have encoded thereon a server program for controlling operation of server 752. In such embodiments, processor 812 can execute at least a portion of the server program to transmit information and/or content (e.g., data, images, a user interface) to one or more computing devices 750, receive information and/or content from one or more computing devices 750, receive instructions from one or more devices (e.g., a personal computer, a laptop computer, a tablet computer, a smartphone), and so on.

In some embodiments, image/data source 702 can include a processor 822, one or more image acquisition systems 824, one or more communications systems 826, and/or memory 828. In some embodiments, processor 822 can be any suitable hardware processor or combination of processors, such as a CPU, a GPU, and so on. In some embodiments, the one or more image acquisition systems 824 are generally configured to acquire data, images, or both, and can include a medical imaging system. Additionally or alternatively, in some embodiments, one or more image acquisition systems 824 can include any suitable hardware, firmware, and/or software for coupling to and/or controlling operations of a medical imaging system. In some embodiments, one or more portions of the one or more image acquisition systems 824 can be removable and/or replaceable.

Note that, although not shown, image/data source 702 can include any suitable inputs and/or outputs. For example, image/data source 702 can include input devices and/or sensors that can be used to receive user input, such as a keyboard, a mouse, a touchscreen, a microphone, a trackpad, a trackball, and so on. As another example, image/data source 702 can include any suitable display devices, such as a computer monitor, a touchscreen, a television, etc., one or more speakers, and so on.

In some embodiments, communications systems 826 can include any suitable hardware, firmware, and/or software for communicating information to computing device 750 (and, in some embodiments, over communication network 754 and/or any other suitable communication networks). For example, communications systems 826 can include one or more transceivers, one or more communication chips and/or chip sets, and so on. In a more particular example, communications systems 826 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 828 can include any suitable storage device or devices that can be used to store instructions, values, data, or the like, that can be used, for example, by processor 822 to control the one or more image acquisition systems 824, and/or receive data from the one or more image acquisition systems 824; to images from data; present content (e.g., images, a user interface) using a display; communicate with one or more computing devices 750; and so on. Memory 828 can include any suitable volatile memory, non-volatile memory, storage, or any suitable combination thereof. For example, memory 828 can include RAM, ROM, EEPROM, one or more flash drives, one or more hard disks, one or more solid state drives, one or more optical drives, and so on. In some embodiments, memory 828 can have encoded thereon, or otherwise stored therein, a program for controlling operation of image/data source 702. In such embodiments, processor 822 can execute at least a portion of the program to generate images, transmit information and/or content (e.g., data, images) to one or more computing devices 750, receive information and/or content from one or more computing devices 750, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for providing navigation to an anatomical region of a spinal cord, the method comprising:

(a) accessing anatomical measurement data with a computer system, the anatomical measurement data including at least one of quantitative dimensions of spinal cord anatomy structures and quantitative dimensions between spinal cord anatomy structures;

(b) accessing medical image data with the computer system, wherein the medical image data were obtained from a subject and depict at least a spinal cord of the subject and one or more vertebrae of the subject, wherein the one or more vertebrae comprise bony landmarks visible in the medical image data;

(c) generating navigation data from the anatomical measurement data and the medical image data using the computer system to map the anatomical measurement data to the medical image data relative to the one or more vertebrae depicted in the medical image data by correlating the anatomical measurement data with the bony landmarks visible in the medical image data to establish spatial relationships between the anatomical measurement data and the vertebrae depicted in the medical image data, wherein the navigation data provide navigation to an anatomical region of the spinal cord by mapping the quantitative dimensions of spinal cord anatomy structures and quantitative dimensions between spinal cord anatomy structures with respect to the one or more vertebrae of the subject, wherein the navigation data comprise spatial location information that indicates positions of spinal cord structures relative to the one or more vertebrae to enable localization of the anatomical region; and (d) displaying the navigation data to a user in order to provide navigation to the anatomical region.

2. The method of claim 1, wherein the navigation data comprise coordinate data for a surgical navigation system.

3. The method of claim 2, wherein the navigation data indicate one or more spatial locations for positioning an electrode for providing electrical stimulation to the spinal cord of the subject.

4. The method of claim 1, wherein the navigation data indicate spatial locations of spinal cord structures relative to the one or more vertebrae depicted in the medical image data.

5. The method of claim 1, wherein the navigation data providing navigation to the anatomical region comprises at least one of a spinal cord segment target, a spinal cord midline target, a spinal cord lateral target, a dorsal column target, a dorsal horn target, a dorsal root entry zone target, an inter-dorsal root entry zone target, and a dorsal rootlet target.

6. The method of claim 1, wherein displaying the navigation data to a user provides navigation of a spinal cord stimulation lead to the anatomical region.

7. The method of claim 1, further comprising generating presurgical planning data with the computer system using the navigation data.

8. The method of claim 1, wherein the anatomical measurement data comprise measurements associated with at least one of dorsal roots or ventral roots.

9. The method of claim 8, wherein the anatomical measurement data comprise at least one of rostral rootlet angle data, caudal rootlet angle data, a number of rootlets, a width across one or more spinal cord columns, or root diameter.

10. The method of claim 1, wherein the anatomical measurement data comprise measurements associated with one or more spinal cord structures.

11. The method of claim 10, wherein the anatomical measurement data comprise at least one of transverse diameter, rostral rootlet to caudal rootlet length, segment length at dorsal column, segment length at bone entry, inferior articular facet to caudal rootlet distance, intervertebral foramen to rostral rootlet distance, or intervertebral foramen to caudal rootlet distance.

12. The method of claim 1, wherein the anatomical measurement data comprise measurements associated with vertebral bones.

13. The method of claim 12, wherein the anatomical measurement data comprise at least one of mid-vertebral foramen length, vertebral bone length, intervertebral foramen distance, or intervertebral foramen diameter.

14. A method for generating augmented spinal cord anatomy model data, the method comprising:

(a) accessing anatomical measurement data with a computer system, the anatomical measurement data including at least one of quantitative dimensions of spinal cord anatomy structures and quantitative dimensions between spinal cord anatomy structures;

(b) accessing medical image data obtained from a subject with the computer system, wherein the medical image data depict at least a spinal cord of the subject and one or more vertebrae of the subject, wherein the one or more vertebrae comprise bony landmarks visible in the medical image data; and (c) generating augmented spinal cord anatomy model data with the computer system by mapping the quantitative dimensions of spinal cord anatomy structures and quantitative dimensions between spinal cord anatomy structures based on the anatomical measurement data to the one or more vertebrae based on the medical image data by establishing correlations between the anatomical measurement data and the bony landmarks identified in the medical image data to create spatial associations between the quantitative dimensions and the bony landmarks.

15. The method of claim 14, wherein the medical image data comprise images acquired with multiple different imaging modalities.

16. The method of claim 15, wherein the multiple different imaging modalities include at least two of magnetic resonance imaging (MRI), x-ray imaging, fluoroscopic imaging, computed tomography, positron emission tomography (PET), single-photon emission computed tomography (SPECT), and ultrasound imaging.

17. The method of claim 14, wherein the anatomical measurement data comprise measurements associated with at least one of dorsal roots or ventral roots.

18. The method of claim 17, wherein the anatomical measurement data comprise at least one of rostral rootlet angle data, caudal rootlet angle data, a number of rootlets, a width across one or more spinal cord columns, or root diameter.

19. The method of claim 14, wherein the anatomical measurement data comprise measurements associated with one or more spinal cord structures.

20. The method of claim 19, wherein the anatomical measurement data comprise at least one of transverse diameter, rostral rootlet to caudal rootlet length, segment length at dorsal column, segment length at bone entry, inferior articular facet to caudal rootlet distance, intervertebral foramen to rostral rootlet distance, or intervertebral foramen to caudal rootlet distance.

21. The method of claim 14, wherein the anatomical measurement data comprise measurements associated with vertebral bones.

22. The method of claim 21, wherein the anatomical measurement data comprise at least one of mid-vertebral foramen length, vertebral bone length, intervertebral foramen distance, or intervertebral foramen diameter.

23. The method of claim 14, further comprising generating surgical navigation data based on the augmented spinal cord anatomy model data.

24. The method of claim 23, wherein the surgical navigation data comprise coordinate data for a surgical navigation system.

25. The method of claim 24, wherein the surgical navigation data indicate one or more spatial locations for positioning an electrode for providing electrical stimulation to the spinal cord of the subject.

26. The method of claim 14, further comprising generating stimulation parameters using the augmented spinal cord anatomy model data, the stimulation parameters indicating settings for a spinal cord stimulation system for delivering electrical stimulation to the spinal cord of the subject.

27. The method of claim 14, further comprising selecting an electrode configuration for delivering spinal cord stimulation to the subject based on the augmented spinal cord anatomy model data.

28. The method of claim 27, wherein selecting the electrode configuration includes at least one of selecting a number of electrodes, a location for placing an electrode, or a type of electrodes to use for delivering the spinal cord stimulation to the subject.

29. The method of claim 14, further comprising displaying the augmented spinal cord anatomy model data to a user.

30. The method of claim 29, wherein displaying the augmented spinal cord anatomy model data to the user comprises displaying the augmented spinal cord anatomy model data together with one or more images contained in the medical image data.

31. The method of claim 30, wherein displaying the augmented spinal cord anatomy model data comprises overlaying the augmented spinal cord anatomy model data with the one or more images contained in the medical image data.

32. The method of claim 29, wherein displaying the augmented spinal cord anatomy model data comprises generating a graphical user interface (GUI) and presenting the augmented spinal cord anatomy model data to the user in conjunction with the GUI.

* * * * *